(12) United States Patent
Burton et al.

(10) Patent No.: US 12,004,816 B2
(45) Date of Patent: Jun. 11, 2024

(54) ROBOTIC SURGICAL APPARATUS WITH POSITIONING GUIDE

(71) Applicant: DePuy Ireland Unlimited Company, Ringaskiddy (IE)

(72) Inventors: Andrew Burton, Raynham, MA (US); François Stéphane Urvoy, Gières (FR)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 804 days.

(21) Appl. No.: 16/834,656

(22) Filed: Mar. 30, 2020

(65) Prior Publication Data

US 2021/0298831 A1 Sep. 30, 2021

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/37* (2016.02); *A61B 90/30* (2016.02);
(Continued)

(58) Field of Classification Search
CPC ... A61B 2034/107; A61B 34/10; A61B 34/20; A61B 34/30; A61B 34/37; A61B 90/13; A61B 90/30; A61B 90/361; A61B 90/92
See application file for complete search history.

(56) References Cited

U.S. PATENT DOCUMENTS 6,450,978 B1 9/2002 Brosseau et al.
6,470,207 B1 10/2002 Simon et al.
(Continued)

FOREIGN PATENT DOCUMENTS

AU 2005237479 B2 11/2005
AU 2007351804 B2 10/2008
(Continued)

OTHER PUBLICATIONS

Brainlab AG, Knee 3 Surgical Technique, Jun. 2015, Rev. 1, https://www.brainlab.com/wp-content/uploads/2016/12/Knee3-Surgical-Technique.pdf.
(Continued)

*Primary Examiner* — Christopher L Cook
(74) *Attorney, Agent, or Firm* — Etan S. Chatlynne; Calderon Safran & Wright, P.C.

(57) ABSTRACT

A robotic surgical apparatus comprises a robot body, a lighting structure, e.g., a light ring, disposed on the robot body, an end effector connected to the robot body, and a robot navigation device connected to the robot body. The robotic surgical apparatus is a component of a robotic surgical system that includes a spatial-data acquisition device. The robotic surgical system assists a user to position the robotic surgical apparatus such that the robotic surgical apparatus may then assist the user to perform a surgical procedure. The lighting structure may be illuminated with a lighting configuration that provides a directional indication from the location of the robotic surgical apparatus toward the target location, and based on the directional indication, the user may move the robotic surgical apparatus along the direction to another location that is closer to the target location.

15 Claims, 5 Drawing Sheets

(51) Int. Cl.
  *A61B 34/37*   (2016.01)
  *A61B 90/00*   (2016.01)
  *A61B 90/30*   (2016.01)

(52) U.S. Cl.
  CPC ...... *A61B 90/361* (2016.02); *A61B 2034/107* (2016.02)

(56) References Cited

U.S. PATENT DOCUMENTS

| | | |
|---|---|---|
| 6,711,432 B1 | 3/2004 | Krause et al. |
| 6,990,220 B2 | 1/2006 | Ellis et al. |
| 7,167,738 B2 | 1/2007 | Schweikard et al. |
| 7,203,277 B2 | 4/2007 | Birkenbach et al. |
| 7,594,933 B2 | 9/2009 | Kammerzell et al. |
| 7,636,595 B2 | 12/2009 | Marquart et al. |
| 7,678,147 B2 | 3/2010 | Clifford et al. |
| 7,699,793 B2 | 4/2010 | Götte et al. |
| 7,715,602 B2 | 5/2010 | Richard |
| 7,835,778 B2 | 11/2010 | Foley et al. |
| 7,905,924 B2 | 3/2011 | White |
| 7,974,677 B2 | 7/2011 | Mire et al. |
| 8,078,440 B2 | 12/2011 | Otto et al. |
| 8,126,533 B2 | 2/2012 | Lavallee |
| 8,295,909 B2 | 10/2012 | Goldbach |
| 8,323,290 B2 | 12/2012 | Metzger et al. |
| 8,382,765 B2 | 2/2013 | Axelson et al. |
| 8,571,637 B2 | 10/2013 | Sheffer et al. |
| 8,706,197 B2 | 4/2014 | Henning et al. |
| 8,888,782 B2 | 11/2014 | Smith et al. |
| 8,894,714 B2 | 11/2014 | Makower et al. |
| 9,498,231 B2 | 11/2016 | Haider et al. |
| 9,852,268 B2 | 12/2017 | Gotte |
| 10,105,149 B2 | 10/2018 | Haider et al. |
| 10,191,302 B2 | 1/2019 | Bailey et al. |
| 10,452,238 B2 | 10/2019 | Nikou et al. |
| 10,987,175 B2 * | 4/2021 | Britton ................ A61B 34/30 |
| 2002/0198451 A1 | 12/2002 | Carson |
| 2003/0069591 A1 | 4/2003 | Carson et al. |
| 2003/0176783 A1 | 9/2003 | Hu |
| 2007/0016008 A1 | 1/2007 | Schoenefeld |
| 2009/0264737 A1 | 10/2009 | Haechler et al. |
| 2010/0153081 A1 | 6/2010 | Bellettre et al. |
| 2014/0324403 A1 | 10/2014 | Gotte |
| 2016/0331474 A1 | 11/2016 | Lacal et al. |
| 2018/0079090 A1 * | 3/2018 | Koenig ................ G01L 3/14 |
| 2019/0049254 A1 * | 2/2019 | Katami ................ G01C 21/20 |
| 2019/0290370 A1 | 9/2019 | Brummund et al. |
| 2020/0100860 A1 * | 4/2020 | Hollopeter ............ A61B 90/08 |
| 2020/0315711 A1 * | 10/2020 | Richter ................ A61B 34/20 |
| 2021/0290315 A1 * | 9/2021 | Lampert ............... A61B 6/032 |
| 2021/0353311 A1 * | 11/2021 | Lavallee ............... A61B 90/11 |

FOREIGN PATENT DOCUMENTS

| | | |
|---|---|---|
| CA | 2 706 356 C | 3/2017 |
| CA | 2 715 315 C | 4/2017 |
| CN | 102985025 A | 3/2013 |
| DE | 100 31 887 A1 | 1/2002 |
| DE | 102 15 808 B4 | 2/2005 |
| DE | 600 32 475 T2 | 9/2007 |
| DE | 10 2016 202 578 A1 | 8/2017 |
| EP | 1 226 788 A1 | 7/2002 |
| EP | 1 153 572 B1 | 8/2002 |
| EP | 1 832 230 B1 | 8/2010 |
| EP | 1 836 978 B1 | 7/2011 |
| EP | 2 654 593 * | 10/2013 |
| EP | 2 044 884 B1 | 12/2015 |
| EP | 2 787 887 B1 | 2/2016 |
| EP | 3 549 553 A3 | 1/2020 |
| ES | 2 216 789 T3 | 11/2004 |
| ES | 2 228 043 T3 | 4/2005 |
| FR | 2 895 267 A1 | 6/2007 |
| JP | 3990719 B2 | 10/2007 |
| JP | 43720000 B2 | 11/2009 |
| KR | 10-0747138 B1 | 8/2007 |
| KR | 10-1660904 B1 | 9/2016 |
| WO | 2004/017836 A2 | 3/2004 |
| WO | 2004/032780 A1 | 4/2004 |
| WO | 2006/092600 A1 | 9/2006 |
| WO | 2007/067150 A1 | 6/2007 |
| WO | 2007/106172 A1 | 9/2007 |
| WO | 2013/052187 A3 | 4/2013 |
| WO | 2013/083297 A1 | 6/2013 |
| WO | 2013/177675 A1 | 12/2013 |
| WO | 2017/179075 A1 | 10/2017 |
| WO | 2019/139935 A1 | 7/2019 |

OTHER PUBLICATIONS

PCT Invitation to Pay Additional Fees and Where Applicable, Protest Fee and Annex to Form PCT/ISA/206 Communication related to the Results of the Partial International Search Report for PCT/EP2021/05817515 dated Jul. 6, 2021, 15 Pages.

* cited by examiner

ROBOTIC SURGICAL APPARATUS WITH POSITIONING GUIDE

FIELD

The subject matter disclosed herein relates to equipment and techniques for performing robotic surgery.

BACKGROUND

Automated or remote-controlled surgical devices, including robots, are used in conducting various surgical procedures to perform functions that may be difficult for a human surgeon to perform. For example, in minimally invasive procedures where surgical instruments are inserted into body cavities through small incisions cut in a subject's tissue, e.g., laparoscopic procedures, automated or remote-controlled devices, particularly those associated with a visualization system, have been used to facilitate manipulation of tissues in the cavity.

SUMMARY OF THE DISCLOSURE

A robotic surgical apparatus comprises a robot body, a lighting structure disposed on the robot body, an end effector connected to the robot body, and a robot navigation device connected to the robot body. The lighting structure may comprise a plurality of light sources, e.g., LEDs, and may be configured in an annular shape, such as a light ring. The robotic surgical apparatus is a component of a robotic surgical system that further comprises a non-transitory storage medium, a processor, and a camera. The robotic surgical apparatus, the non-transitory storage medium, and the camera may be connected to the processor.

The robotic surgical system assists a user, e.g., surgeon or healthcare professional, to position the robotic surgical apparatus such that the robotic surgical apparatus may then assist the user to perform a surgical procedure. Accordingly, the robotic surgical system may be used to conduct a method with steps of defining a coordinate system representative of a procedural field having a reference point, defining a target location in the coordinate system representative of a target location in the procedural field, defining a location of the robotic surgical apparatus in the coordinate system representative of a location of the robotic surgical apparatus in the procedural field, illuminating the lighting structure with a lighting configuration that provides a directional indication of a direction from the location of the robotic surgical apparatus in the procedural field toward the target location in the procedural field, and based on the directional indication, moving the robotic surgical apparatus along the direction to another location in the procedural field that is closer to the target location in the procedural field than the location of the robotic surgical apparatus in the procedural field. These steps may be repeated until the robotic surgical apparatus is positioned at the target location.

As used herein, the term "navigation device" refers to any device, structure, component, assembly, apparatus, or system that may be associated with a physical object for the purpose of enabling a prompt detection of the location of the physical object by a navigation system (e.g., visual imaging systems, thermographic imaging systems, electromagnetic imaging systems) or a larger system, such as the robotic surgical system described herein, that comprises an imaging system (and in the specific disclosed embodiments comprises a visual imaging system including a camera, a processor, and a storage medium). Examples of navigation devices may include, but are not limited to, position sensors, antennas, navigation arrays, gyroscopes, and accelerometers.

As used herein, the term "image" or "images" encompasses images including, but not limited to, photographic images taken by a camera or a video camera, thermographic images (e.g., an image based on infrared energy of physical structures) taken by a thermographic camera (e.g., an infrared camera that is operable to detect and measure infrared energy from physical structures), or any other representation of physical structures, including two-dimensional or three-dimensional spatial information regarding the physical structures based on data collected by non-photographic devices (e.g., electromagnetic position sensors or mapping sensors), as well as electronic media (e.g., digital photographs and computer-aided designs) that may be displayed on an electronic display (e.g., computer monitor, laptop screen, tablet, electronic paper, e-reading device) or otherwise provided or printed in a manner involving non-electronic media (e.g., paper or physical prototype, such as 3D printing).

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host,"

"user," and "subject" refer to any human or animal subject and are not intended to limit the systems or methods to human use, although use of the subject invention in a human patient represents a preferred embodiment.

Figure 1:
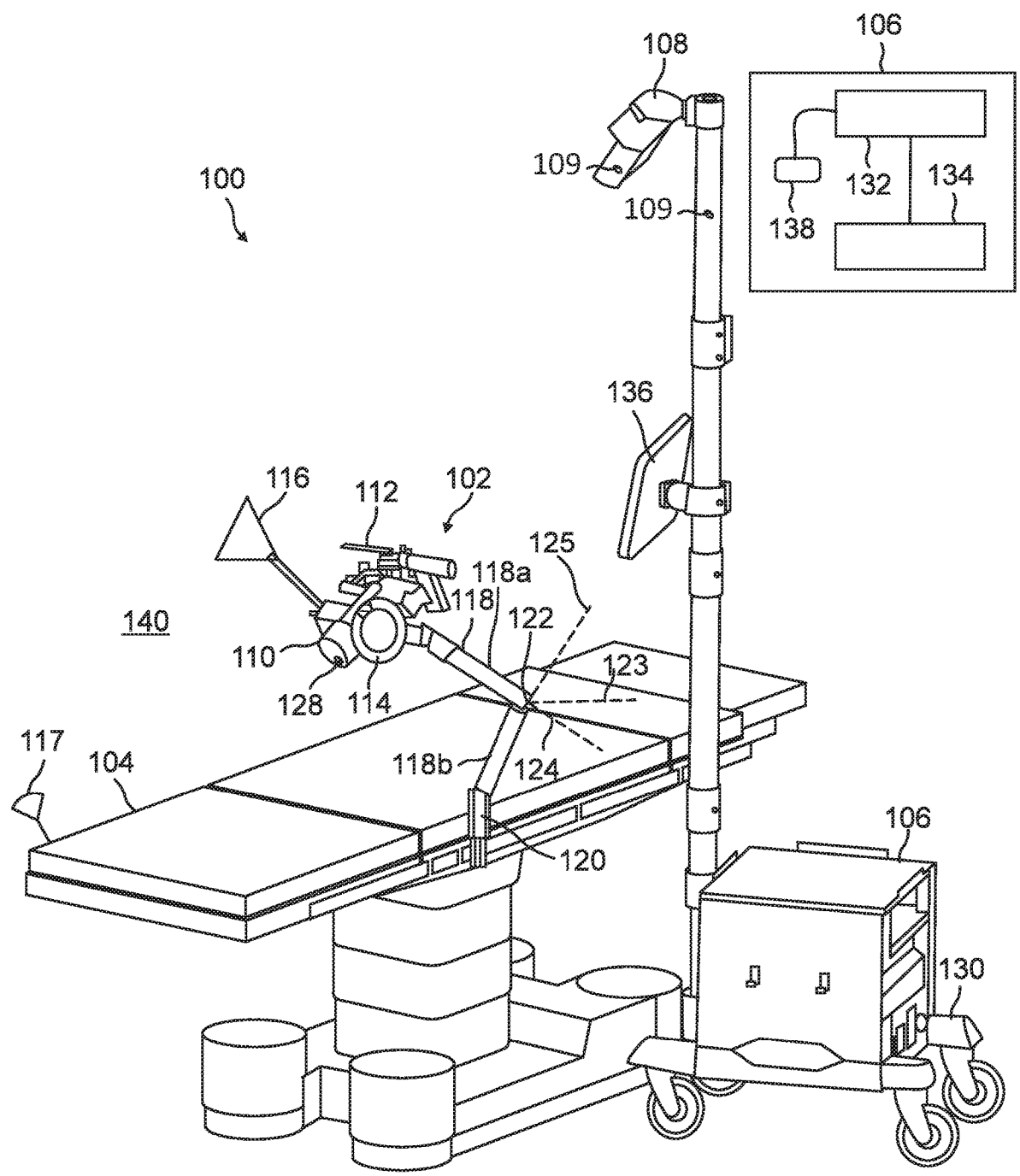
FIG. 1 depicts a robotic surgical system.

FIG. 1 reflects a robotic surgical system 100 that includes, among other things, a robotic surgical apparatus 102, a surgical bed 104, an operating console 106, and a spatial-data acquisition device (e.g., camera 108). Robotic surgical apparatus 102 may be used to assist in conducting a surgical procedure by, e.g., performing various steps of the procedure, such as cutting bone. In surgical procedures, e.g., knee-replacement surgical procedures, where a bone is cut to prepare the bone to receive a prosthesis, the robotic surgical apparatus 102 may perform the cuts with increased precision relative to a human surgeon.

Robotic surgical apparatus 102 includes a robot body 110, an end effector (e.g., saw, burr, cannula, drill, retractor) 112, a position guide or lighting structure 114, a robot navigation device 116, and a positioning arm 118. Lighting structure 114 is provided to provide directional feedback to a user, e.g., surgeon or technician, intended to assist the user in moving apparatus 102 to a target location, e.g., proximate to a subject's knee. Lighting structure 114 may provide feedback in two dimensions or three dimensions. Two-dimensional feedback may be appropriate where the robot is restricted to movement within a plane. In these instances, lighting structure 114 may comprise a light ring. Three-dimensional feedback may be appropriate where the robot is not restricted to movement within a plane. In these instances, lighting structure 114 may comprise a light cylinder or a light cube. Various light sources may be disposed inside of lighting structure 114 and be arranged at or proximate to the outer edges of lighting structure 114. The light sources may be individual light bulbs or LEDs, such as multi-color LEDs. Preferably, many light sources are provided about lighting structure 114 such that illumination of a uniform intensity may be provided about the entirety of lighting structure 114 or any portion thereof. For example, where lighting structure 114 comprises a light ring, there may be one light source per degree, such that 360 light sources are distributed about and inside of light ring 114. Alternatively, there may be one light source per every two degrees, four degrees, etc. Although the light sources are disposed inside of the lighting structure, housing components of the lighting structure are transparent or translucent such that the light sources might not be visible through the housing but light form the light sources may illuminate the lighting structure. In further embodiments robot body 110 may include a sound source (e.g., speaker) 128, which may supplement lighting structure 114 in providing position input to the user.

Robot navigation device 116 is preferably connected to robot body 110 in a rigid manner such that the spatial relationship between robot navigation device 116 and robot body 110 is fixed. Robot navigation device 116 may simplify determining the position of robot body 110 by operating console 106, the spatial data acquisition device (e.g., camera 108), or both working in conjunction, as will be explained below. Robot navigation device 116 may comprise an active element, e.g., an element that includes an infrared emitting element, such as an infrared LED. Alternatively or additionally, robot navigation device 116 may comprise an infrared reflecting material, such as aluminum. Alternatively or additionally, robot navigation device 116 may comprise an infrared absorbing material, such as glass.

Robotic surgical apparatus 102 may also include a fastening device (e.g., clamp) 120 connected to the robot body. Fastening device 120 may be used to fasten apparatus 102 to bed 104. Fastening device 120 may be connected to robot body 110 by an arm 118. Arm 118 may comprise a first portion 118a and a second portion 118b connected by a joint 122. Joint 122 may permit first portion 118a and second portion 118b to be articulated relatively to each other to assist in positioning robot body 110 at many more locations than if arm 118 could not so articulate. As such, joint 122 may define a rotational axis 123 about which first portion 118a and second portion 118b may be rotated. Additionally, first portion 118a may be rotated about a longitudinal axis 124 of first portion 118a, and second portion 118b may be rotated about a longitudinal axis 125 of second portion 118b. Further, each one of these rotations may be accomplished independently of any of other rotations of 118a or 118b. Preferably, joint 122 includes sufficient internal friction or a clamping mechanism that maintains the positions of portions 118a and 118b when they are not being manipulated by a user.

Robotic surgical system 100, as noted above, additionally includes operating console 106 and a spatial-data acquisition device (e.g., camera 108). In an exemplary form, console 106 and camera 108 may be provided as a single apparatus, e.g., with operating console 106 and camera 108 secured to a wheeled cart or dolly 130. Additionally, a user interface 136 may be provided that may be used to display images of a procedural field 140 captured by camera 108 and that may further be used to collect inputs from and display outputs to the user. Camera 108 and user interface 136 may further be disposed on a rod, which may have a telescoping functionality, which may assist in at least positioning camera 108.

Camera 108 may comprise one or more cameras, e.g., thermographic cameras, such as infrared cameras. Camera 108 may further comprise sources of infrared energy 109, such as infrared diodes or LEDs. Alternatively or additionally, such sources of infrared energy 109 may be provided separately from cameras 108, e.g., elsewhere on support 130. Infrared energy provided from one or more sources 109 may be reflected by structures in the procedural field, such as at least one of the various navigation devices described herein (i.e., 116, 117). Camera 108 receives and records the reflected infrared energy as data, e.g., one or more infrared images, which thus comprises spatial data. Camera 108 then provides these data as inputs to processor 132 either directly or indirectly via an initial delivery of the data to storage medium 134 such that processor 132 may subsequently retrieve the data from storage medium 134.

Alternatively or additionally, robotic surgical system 100 may include a navigation or mapping system for determining positions of navigation devices 116 and 117 without use of visual or thermographic images. As such, the spatial-data acquisition device need not be a camera. Rather, other types of spatial-data acquisition devices, e.g., position sensors, may be employed. For example, the position sensors may be a set of three non-concentric coils that, when disposed in an externally applied magnetic field, have currents induced therethrough. The currents in the three coils of any such three-coil set comprise spatial data and may be provided as inputs to the processor or to storage medium 134 such that processor 132 may subsequently retrieve the data from storage medium 134. The processor may analyze the data to determine three degrees of position and three degrees of orientation for any such three-coil set in each navigation array. Such analysis and determination may be performed continuously.

As reflected in the schematic representation of operating console 106 in FIG. 1, operating console includes at least a processor 132 a non-transitory storage medium 134, and, optionally, a sound source 138, each of which may be provided for by a digital computer. Non-transitory storage medium 134 may be, e.g., random access memory (RAM), a hard-disk drive, or flash memory or any other non-transitory storage medium which can store software or logic that processor 132 may execute to operate robotic surgical system 100 and process spatial data collected by spatial-data acquisition device, such as images captured by camera 108. These operations are detailed below. Robotic surgical apparatus 102 and the spatial-data acquisition device (e.g., camera 108) may be connected to operating console 106 by wire (e.g., cable) or wirelessly (e.g., Wi-Fi or Bluetooth) such that processor 132 may receive inputs from and provide outputs to the spatial-data acquisition device (e.g., camera 108) and robotic surgical apparatus 102. Sound source 138, may be used to provide feedback to the user. As such, sound source 138 may be a speaker.

Another navigation device, e.g., a reference navigation device 117, may be positioned anywhere in the procedural field 140 (i.e., within the field of view of camera 108). As shown in FIG. 1, reference navigation device 117 is attached to bed 104. Reference navigation device 117 may be of a similar design to robot navigation device 116. Reference navigation device 117 may be utilized by system 100 to define a coordinate system representative of procedural field 140 whereby the position of reference navigation device 117 in procedural field 140 may correspond the origin of the coordinate system.

Figure 2:
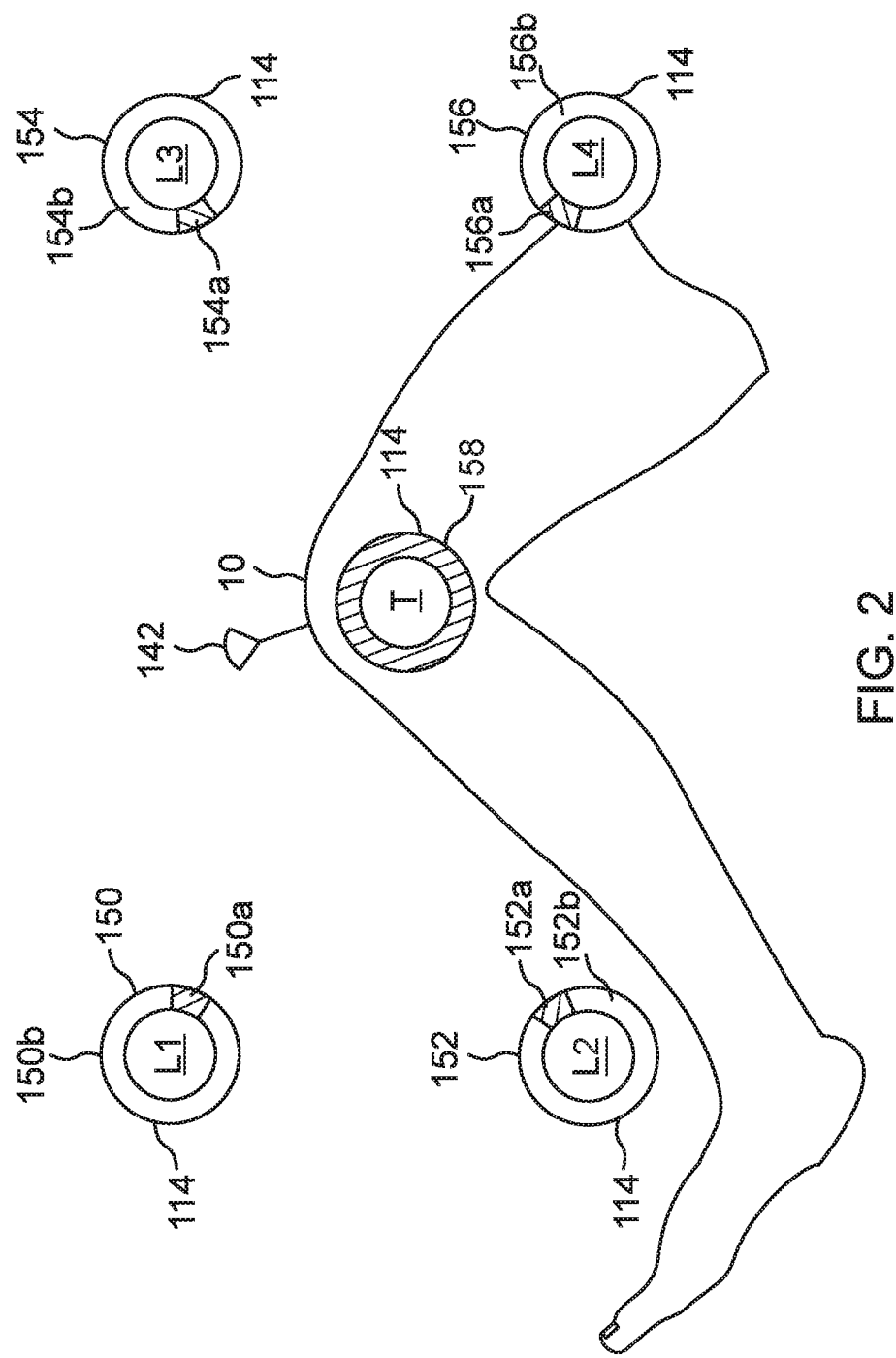
FIG. 2 depicts a lighting structure of the robotic surgical system positioned at various locations in a procedural field and illuminated in various lighting configurations.
Figure 3:
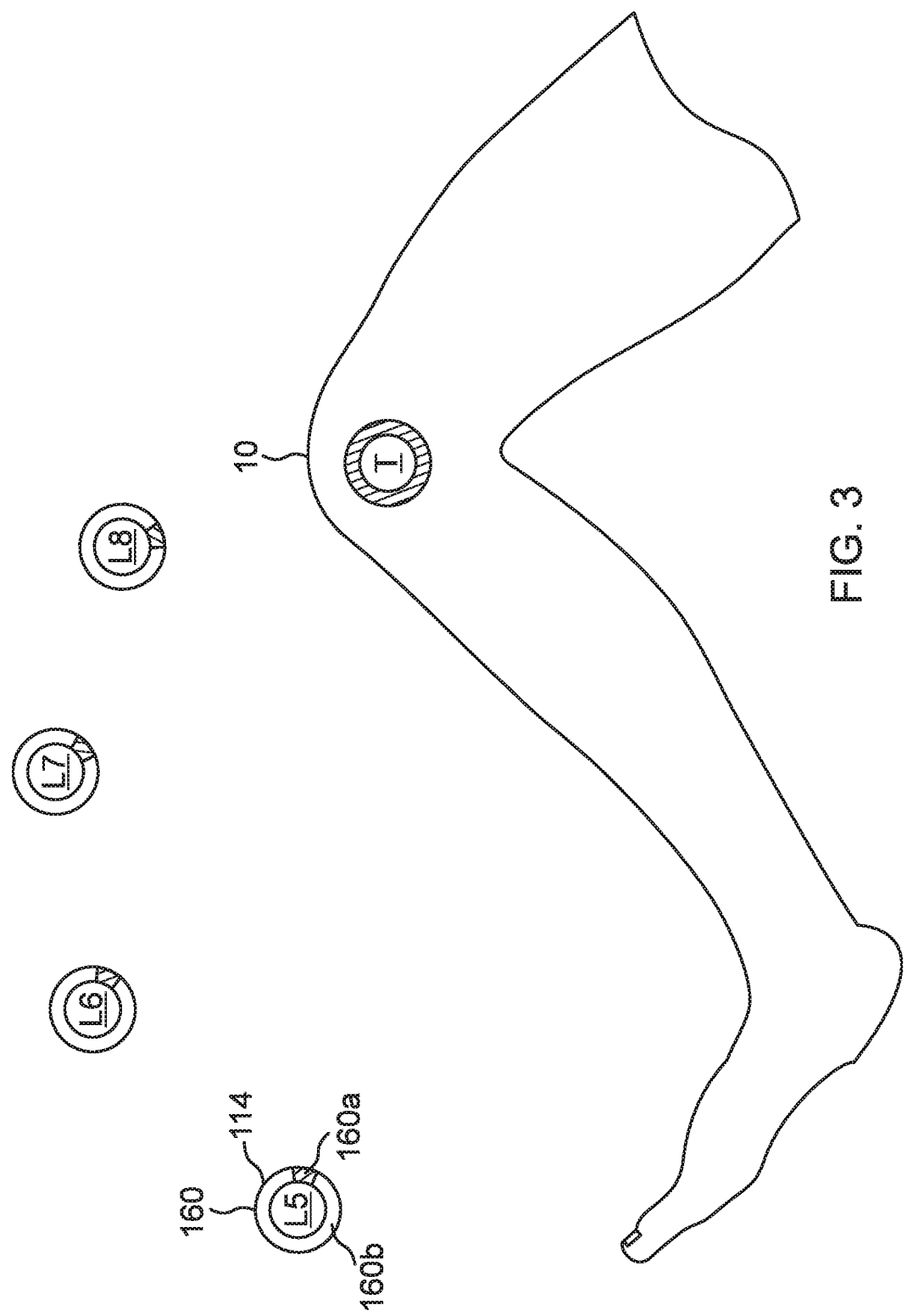
FIG. 3 depicts the lighting structure of the robotic surgical system positioned at various locations in a procedural field and illuminated in various lighting configurations.
Figure 4:
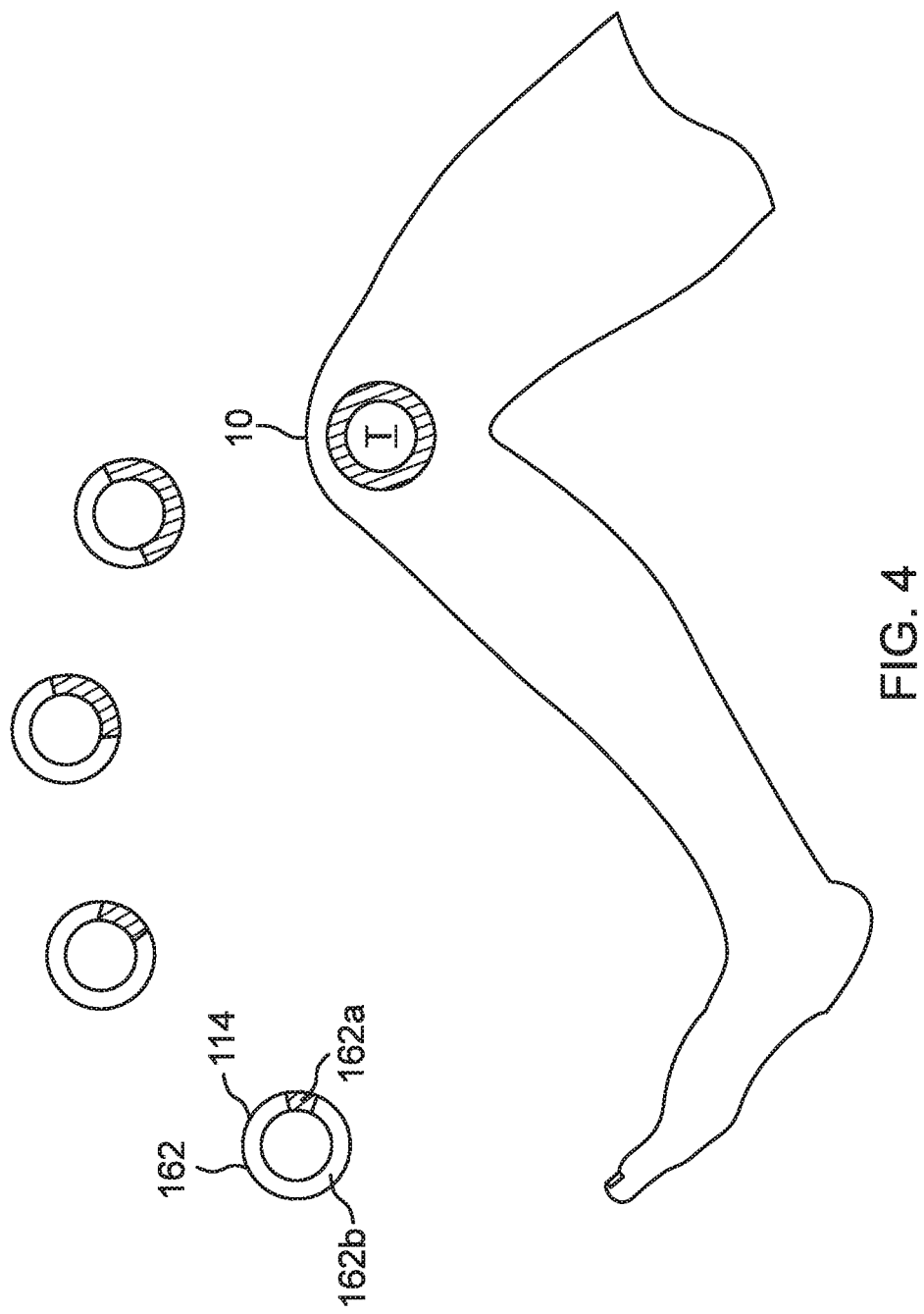
FIG. 4 depicts the lighting structure of the robotic surgical system positioned at various locations in a procedural field and illuminated in various lighting configurations.
Figure 5:
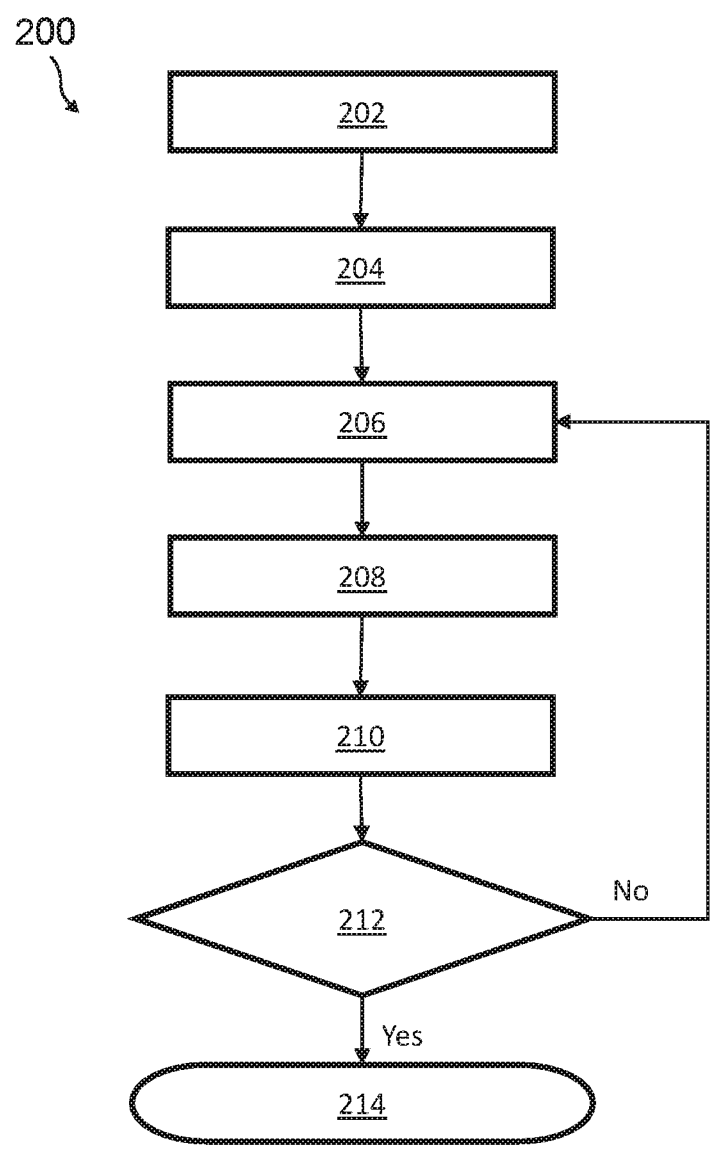
FIG. 5 depicts a flow chart reflecting a method for positioning a robotic surgical apparatus of the robotic surgical system.

Robotic surgical system 100 may be used to, among other things, assist a user in positioning robot body 110 at a target location such that robotic surgical apparatus 102 may subsequently assist in performing steps of a surgical procedure, such as steps that include resecting bone. For example, robotic surgical apparatus 102 may assist in performing steps of a knee-replacement procedure by assisting a user to position apparatus 102 at a target location proximate to a subject's knee. FIGS. 2-4 provide examples of how system 100 may assist in such positioning relative to a subject's knee 10 after the subject has been positioned on bed 104 of FIG. 1. In these examples, knee 10 may be regarded as a target location, or, more specifically, the target location may be a location just lateral of the knee 10 such that, when robot body 110 is positioned at the target location, end effector 112 may be extended to reach and one or more bones of knee 10. Another navigation device, e.g., a target navigation device 142, may be positioned proximate to the target location, i.e., knee 10, in procedural field 140, which may simplify determining the position of the target location by operating console 106, camera 108, or both, as explained below.

FIGS. 2-4 each reflect lighting structure 114 at various locations in a procedural field. For clarity, the only feature of robotic surgical apparatus 102 shown in FIGS. 2-5 is lighting structure 114. For the avoidance of a doubt, however, Applicant notes that lighting structure 114 is disposed on robot body 110 of robotic surgical apparatus 102 as reflected in FIG. 1, and that lighting structure 114 along with robot body 110 may only be positioned in one location at a time. In FIG. 2, lighting structure is shown as it might appear when robotic surgical apparatus 102 is positioned at five different locations (i.e., at different times) relative to knee 10, e.g., in a plane disposed parallel and lateral to the subject's leg. These locations are identified in FIG. 2 as L1, L2, L3, L4, and T. L1 is a location that is anterior and inferior to knee 10. L2 is a location that is posterior and inferior to knee 10. L3 is a location that is anterior and superior to knee 10. L4 is a location that is posterior and superior to knee 10. Finally, T may be regarded as a target location in front of—or lateral to—knee 10. As noted above, lighting structure 114 may comprise various light sources, e.g., LEDs. These light sources may be set to various lighting configurations based on the location at which robotic surgical apparatus 102 is positioned. For example, when apparatus 102 is positioned at L1, lighting structure 114 may be set to lighting configuration 150, in which illuminated portion 150a is closer to location T than the non-illuminated portion 150b. When apparatus 102 is positioned at L2, lighting structure 114 may be set to lighting configuration 152, in which illuminated portion 152a is closer to location T than the non-illuminated portion 152b. When apparatus 102 is positioned at L3, lighting structure 114 may be set to lighting configuration 154, in which illuminated portion 154a is closer to location T than the non-illuminated portion 154b. When apparatus 102 is positioned at L4, lighting structure 114 may be set to lighting configuration 156, in which illuminated portion 156a is closer to location T than the non-illuminated portion 156b. Accordingly, as apparatus 102 is moved relative to knee 10, the illuminated portion of lighting structure 114 correspondingly moves. Because the illuminated portions are closer to T than the respective non-illuminated portion at each of the other locations, it may be considered that the illuminated portions point toward location T along a direction from the illuminated portion to T. Accordingly, lighting structure 114 provides functionality similar to a magnetic compass, which includes a needle that points toward magnetic north irrespective of the location and orientation of the compass itself. In this manner, lighting structure 114 communicates to a user a direction in which apparatus 102 should be moved in order to reach the target location T. Ultimately, upon positioning apparatus 102 at T, i.e., the target location, the lighting structure 114 may be set to lighting configuration 158 to indicate that apparatus 102 has been positioned at the target location. For example, as shown in FIG. 2, the entirety of lighting structure 114 when positioned at target T is illuminated in lighting configuration 158 such that there is no non-illuminated portion.

FIG. 3 reflects a progression of how the lighting configuration 160 of lighting structure 114 could change in response to apparatus 102 being moved from location L5 to location L6 to location L7 to location L8, and finally to target location T. Irrespective of the location of apparatus 102 (excluding when the apparatus is at the target location), the illuminated portion 160a is always closer to the target location than the non-illuminated portion 160b.

FIG. 4 reflects a similar technique as FIG. 3, but with lighting configuration 162 changing to provide an additional indication of proximity. As shown, as the distance between apparatus 102 and the target location decreases, the size of the illuminated portion 162a grows relative to the non-illuminated portion 162b.

In any of the foregoing lighting-configuration examples, the portions that are explained as being illuminated (e.g., 150a) may instead be the non-illuminated portions and the portions that are explained as being non-illuminated (e.g., 150b) may instead be the illuminated portions. Accordingly, in these reversed lighting configurations, the non-illuminated portions would point toward location T.

Furthermore, the lighting configuration may further include blinking the light sources to communicate information to a user. For example, slow blinking may indicate that the robotic surgical apparatus is far from the target location, fast blinking may indicate that the robotic surgical apparatus is close to the target location, and continuous illumination (i.e., no blinking) may indicate that the apparatus is positioned at the target location.

System 100 may also provide audible feedback to a user via sound source 128 or 138. For example a slow beeping or low-pitch beep may indicate that the robotic surgical apparatus is far from the target location, fast beeping or a high-pitch beep may indicate that the robotic surgical apparatus is close to the target location, and a continuous sound or vocalized words (e.g., "the target has been reached") may indicate that the apparatus is positioned at the target location.

By virtue of the embodiments illustrated and described herein, Applicant has devised a method and variations thereof for positioning a robotic surgical apparatus (e.g., apparatus 102) at or proximate to a target location (e.g., knee 10). The method and variations are described below and reflected as method 200 in the flow chart of FIG. 5. Step 202 includes defining a coordinate system that is representative of a procedural field (e.g., procedural field 140), such as an operating room, in which a subject and robotic surgical apparatus 102 are disposed. The coordinate system preferably includes an origin (i.e., coordinate origin) that is representative of a reference point in the procedural field. The reference point may be a point on a table in the procedural field, a wall in the procedural field, or a bone in the procedural field. Identification of the reference point may be facilitated by positioning a reference navigation device at the reference point in the procedural field, such as is reflected in FIG. 1, with reference navigation device 117 attached to bed 104.

Accordingly, step 202 may itself be comprised of the following steps. First, a spatial-data acquisition device (e.g., camera 108) may be used to collect reference spatial data (e.g., a reference image) of the procedural field that includes the reference point and, if being used, the reference navigation device. Then, the reference spatial data may be provided as an input to a processor (e.g., processor 132 of operating console 106). Then the processor may identify the reference point from the reference spatial data, which may include identifying the reference navigation device therefrom. Then, the processor may define the location of the reference point as the origin of the coordinate system.

Step 204 includes defining a target location in the coordinate system that is representative of a target location in the procedural field. Step 204 may itself be comprised of the following steps. First, a target navigation device may optionally be positioned at the target location in the procedural field. For example, as seen in FIG. 2, target navigation device 142 is positioned at knee 10. Then, spatial-data acquisition device (e.g., camera 108) may be used to collect target spatial data (e.g., a target image) of the procedural field that includes the target location. Then, the target spatial data may be provided as an input to the processor. Then the processor may identify the target location, the target navigation device, or both, from the spatial data. Then, the processor may define the target location in the coordinate system as a location in the coordinate system that corresponds to the target location in the procedural field. For example, the processor may determine a distance vector between the reference point and the target location in the procedural field and then may define the target location in the coordinate system as the location defined by adding this distance vector to coordinates of the coordinate system's origin.

Step 206 includes defining a location of the robotic surgical apparatus in the coordinate system that is representative of a location of the robotic surgical apparatus in the procedural field. Step 206 may itself be comprised of the following steps. First, the spatial-data acquisition device may be used to collect spatial data (e.g., an image) that includes at least robot body 110, and preferably also robot array 116, in the procedural field. This spatial data may be referred to herein as robot-location spatial data. Then, the robot-location spatial data may be provided as an input to the processor. Then the processor may identify the robot body, the robot array, or both, from the robot-location spatial data. Then, the processor may define the location of the robotic surgical apparatus in the coordinate system as a location in the coordinate system that corresponds to the location of the robotic surgical apparatus in the procedural field. For example, the processor may determine a distance vector between the reference point and the location of the robotic surgical apparatus in the procedural field and then may define the location of the robotic surgical apparatus in the coordinate system as the location defined by adding this distance vector to coordinates of the coordinate system's origin.

Step 208 includes illuminating a lighting structure (e.g., lighting structure 114) with a lighting configuration that provides a directional indication of a direction from the location of the robotic surgical apparatus in the procedural field toward the target location in the procedural field. Step 208 may itself be comprised of the following steps. First, the processor calculates a directional vector from the location of the robotic surgical apparatus in the coordinate system to the target location in the coordinate system. Then, the processor sends an output signal from the processor to the lighting structure that comprises a set of inputs informing the lighting structure as to whether each light source should be illuminated (i.e., on or turned on) or non-illuminated (i.e., off or turned off). Furthermore, the signal may include inputs as to the color that any illuminated light source should be, e.g., red or blue. In this fashion, red may be used to indicate that the user is "getting hot" as the robotic surgical apparatus is moved closer to the target location whereas blue may be used to indicate that the user is "getting cold" as the robotic surgical apparatus is moved away from the target location.

Step 210 includes moving the robotic surgical apparatus, based on the directional indication, along the direction to another location in the procedural field that is closer to the target location in the procedural field than the prior location of the robotic surgical apparatus in the procedural field.

Step 212 includes determining, with the processor whether the robotic surgical apparatus is positioned at the target location. If yes, the method continues at step 214. If no, then the method returns to step 206 such that steps 206, 208, 210, and 212 may be repeated for the another location of the robotic surgical apparatus. Repetition of step 206 thus results in defining an updated location of the robotic surgical apparatus in the coordinate system that is representative of an updated location of the robotic surgical apparatus in the procedural field. Repetition of step 208 thus results in illuminating the lighting structure with an updated lighting configuration that provides a directional indication of an updated direction from the another location of the robotic surgical apparatus in the procedural field toward the target location in the procedural field. Repetition of step 210 thus results in moving the robotic surgical apparatus from the another location to yet another location.

Step 214 includes repeating the steps of steps 210 and 212 until the robotic surgical apparatus has reached the target location in the procedural field. Such may be performed in a continuous manner, a piecewise manner, or both. For example, repeating steps 210 and 212 in a continuous manner may be preferred when the robotic surgical apparatus is positioned far from the target location, whereas repeating steps 210 and 212 in a piecewise manner may be preferred when the robotic surgical apparatus is almost positioned at the target location. That is, a continuous manner may be preferred when large movements of the apparatus may be preferred whereas the piecewise manner may be preferred when small movements of the apparatus may be preferred.

Step 214 includes providing a signal or indication that the robotic surgical apparatus is positioned at the target location in the procedural field. For example, the light sources may be illuminated in a manner that suggests the target location has been reached, e.g., all of the light sources may be illuminated in green. Alternatively or additionally, a sound may be emitted from a sound source, such as sound source 128 of robotic surgical apparatus 102 or sound source 138 of operating console 106.

Various aspects of the subject matter according to the present disclosure include, but are not limited to, the aspects listed in the following numbered clauses.

1. A robotic surgical apparatus, comprising:
   a robot body;
   a lighting structure disposed on the robot body;
   an end effector connected to the robot body; and
   a robot navigation device connected to the robot body.

2. The robotic surgical apparatus of clause 1, in which the lighting structure comprises a light ring.

3. The robotic surgical apparatus of clause 1, in which the lighting structure comprises a light cylinder.

4. The robotic surgical apparatus of clause 1, in which the lighting structure comprises a light cube.

5. The robotic surgical apparatus of any of the preceding clauses, in which the lighting structure comprises a plurality of light sources disposed about the lighting structure.

6. The robotic surgical apparatus of clause 5, in which each of the plurality of light sources comprises an LED.

7. The robotic surgical apparatus of clause 6, in which each LED comprises a multi-color LED.

8. The robotic surgical apparatus of any of the preceding clauses, in which the robot navigation device is rigidly connected to the robot body.

9. The robotic surgical apparatus of any of the preceding clauses, in which the robot navigation device comprises an active element.

10. The robotic surgical apparatus of any of the preceding clauses, in which the robot navigation device comprises an infrared emitting element.

11. The robotic surgical apparatus of clause 10, in which the infrared emitting element comprises an LED.

12. The robotic surgical apparatus of any of the preceding clauses, in which the robot navigation device comprises an infrared reflecting material.

13. The robotic surgical apparatus of clause 12, in which the infrared reflecting material comprises aluminum.

14. The robotic surgical apparatus of any of the preceding clauses, in which the robot navigation device comprises an infrared absorbing material.

15. The robotic surgical apparatus of clause 14, in which the infrared absorbing material comprises glass.

16. The robotic surgical apparatus of any of the preceding clauses, further comprising a fastening device connected to the robot body.

17. The robotic surgical apparatus of clause 16, in which the fastening device comprises a clamp.

18. The robotic surgical apparatus of clause 16 or 17, further comprising an arm that connects the fastening device to the robot body.

19. The robotic surgical apparatus of clause 18, in which the arm comprises a joint.

20. The robotic surgical apparatus of clause 19, in which the joint connects a first portion of the arm to a second portion of the arm such that the first portion of the arm may be moved independently from the second portion of the arm.

21. The robotic surgical apparatus of clause 20, in which the first portion of the arm may be rotated about a longitudinal axis of the first portion of the arm without moving the second portion of the arm.

22. The robotic surgical apparatus of clause 20 or 21, in which the joint defines a rotational axis about which the first portion of the arm may be rotated without moving the second portion of the arm.

23. The robotic surgical apparatus of any of the preceding clauses, further comprising a sound source connected to the robot body.

24. The robotic surgical apparatus of clause 23, in which the sound source comprises a speaker.

25. A robotic surgical system, comprising:
   the robotic surgical apparatus of any of clauses 1 to 24;
   an operating console comprising a non-transitory storage medium and a processor; and
   a camera,
   in which the robotic surgical apparatus and the camera are connected to the processor.

26. The robotic surgical system of clause 25, in which the robotic surgical apparatus is wirelessly connected to the processor.

27. The robotic surgical system of clause 25 or 26, further comprising a reference navigation device.

28. The robotic surgical system of clause 27, in which the reference navigation device is positioned proximate to a reference point within a view of the camera.

29. The robotic surgical system of any of clauses 25 to 28, further comprising a target navigation device.

30. The robotic surgical system of clause 29, in which the target navigation device is positioned proximate to a target location.

31. The robotic surgical system of clause 30, in which the target location comprises a knee.

32. The robotic surgical system of any of clauses 25 to 31, in which the operating console further comprises a sound source.

33. A method of positioning the robotic surgical apparatus of the robotic surgical system of any of clauses 25 to 32, comprising:
   defining a coordinate system representative of a procedural field having a reference point;
   defining a target location in the coordinate system representative of a target location in the procedural field;
   defining a location of the robotic surgical apparatus in the coordinate system representative of a location of the robotic surgical apparatus in the procedural field;
   illuminating the lighting structure with a lighting configuration that provides a directional indication of a direction from the location of the robotic surgical apparatus in the procedural field toward the target location in the procedural field; and
   based on the directional indication, moving the robotic surgical apparatus along the direction to another location in the procedural field that is closer to the target location in the procedural field than the location of the robotic surgical apparatus in the procedural field.

34. The method of clause 33, further comprising updating the lighting configuration to an updated lighting configuration to provide an updated directional indication of an updated direction from the another location in the procedural field toward the target location in the procedural field.

35. The method of clause 34, further comprising repeating the steps of moving the robotic surgical apparatus and updating the lighting configuration until the robotic surgical apparatus is positioned at the target location in the procedural field.

36. The method of any of clauses 33 to 35, further comprising providing a signal that the robotic surgical apparatus is positioned at the target location in the procedural field.

37. The method of any of clauses 33 to 36, further comprising positioning a reference navigation device at the reference point in the procedural field.

38. The method of any of clauses 33 to 37, in which the reference point comprises a point on a table in the procedural field, a wall in the procedural field, or a bone in the procedural field.

39. The method of any of clauses 33 to 38, in which the step of defining the coordinate system comprises:
using the camera to capture a reference image of the procedural field that includes the reference point;
providing the reference image to the processor;
identifying the reference point in the image with the processor; and
defining an origin representative of the reference point in the procedural field.

40. The method of clause 39, in which the step of identifying the reference point in the image with the processor includes identifying the reference navigation device in the image.

41. The method of any of clauses 33 to 40, further comprising positioning a target navigation device at the target location in the procedural field.

42. The method of clause 41, in which the step of defining the target location in the coordinate system comprises:
using the camera to capture a target image of the procedural field;
providing the target image to the processor;
identifying the target navigation device in the target image with the processor; and
determining the location of the target navigation device in the procedural field with the processor.

43. The method of any of clauses 33 to 42, in which the step of defining the location of the robotic surgical apparatus in the coordinate system comprises:
using the camera to capture a robot-location image of the procedural field;
providing the robot-location image to the processor;
identifying the robot navigation device in the robot-location image with the processor; and
determining the location of the robotic surgical apparatus in the procedural field with the processor.

44. The method of any of clauses 33 to 43, in which the step of illuminating the lighting structure with the lighting configuration comprises:
calculating, with the processor, a directional vector from the location of the robotic surgical apparatus in the coordinate system to the target location in the coordinate system; and
outputting a signal from the processor to the lighting structure that causes the lighting structure to be in the lighting configuration.

45. The method of clause 44, in which the lighting configuration comprises the updated lighting configuration.

46. The method of any of clauses 33 to 45, in which the lighting configuration includes at least one illuminated light source that is disposed closer to the target location in the procedural field than any other light source that is non-illuminated.

47. The method of any of clauses 33 to 45, in which the lighting configuration includes at least one non-illuminated light source that is disposed closer to the target location in the procedural field than any other light source that is illuminated.

48. The method of any of clauses 33 to 45, in which the lighting configuration includes at least one light source that is illuminated in a first color and disposed closer to the target location in the procedural field than any other light source that is illuminated in a second color different than the first color.

49. The method of clause 48, in which all of the light sources are illuminated in either first color or the second color.

50. The method of any of clauses 33 to 49, in which the step of providing the signal that the robotic surgical apparatus is positioned at the target location includes illuminating all of the plurality of light sources.

51. The method of clause 50, in which the step of providing the signal that the robotic surgical apparatus is positioned at the target location includes illuminating all of the plurality of light sources in a third color that is different from the first color and the second color.

52. The method of clause 51, in which the first color comprises blue, the second color comprises red, and the third color comprises green.

53. The method of any of clauses 33 to 52, in which the step of providing the signal that the that the robotic surgical apparatus is positioned at the target location includes emitting a sound from the sound source.

54. A method of positioning a robotic surgical apparatus comprising a lighting structure including a plurality of light sources, the method comprising:
defining a coordinate system representative of a procedural field having a reference point;
defining a target location in the coordinate system representative of a target location in the procedural field;
defining a location of the robotic surgical apparatus in the coordinate system representative of a location of the robotic surgical apparatus in the procedural field;
illuminating the lighting structure with a lighting configuration that provides a directional indication of a direction from the location of the robotic surgical apparatus in the procedural field toward the target location in the procedural field; and
based on the directional indication, moving the robotic surgical apparatus along the direction to another location in the procedural field that is closer to the target location in the procedural field than the location of the robotic surgical apparatus in the procedural field.

55. The method of clause 54, further comprising updating the lighting configuration to an updated lighting configuration to provide an updated directional indication of an updated direction from the another location in the procedural field toward the target location in the procedural field.

56. The method of clause 55, further comprising repeating the steps of moving the robotic surgical apparatus and updating the lighting configuration until the robotic surgical apparatus is positioned at the target location in the procedural field.

57. The method of clause 56, further comprising providing a signal that the robotic surgical apparatus is positioned at the target location in the procedural field.

58. The method of clause 56, further comprising positioning a reference navigation device at the reference point in the procedural field.

59. The method of clause 58, in which the reference point comprises a point on a table in the procedural field, a wall in the procedural field, or a bone in the procedural field.

60. The method of clause 56, in which the step of defining the coordinate system comprises:
using a spatial-data acquisition device to collect reference spatial data of the procedural field that includes the reference point;
providing the reference spatial data to a processor;
identifying the reference point with the processor; and
defining an origin representative of the reference point in the procedural field.

61. The method of clause 60, in which the step of identifying the reference point with the processor includes identifying the reference navigation device.

62. The method of clause 56, further comprising positioning a target navigation device at the target location in the procedural field.

63. The method of clause 62, in which the step of defining the target location in the coordinate system comprises:
using the spatial-data acquisition device to capture target spatial data of the procedural field;
providing the target spatial data to the processor;
identifying the target navigation device with the processor; and
determining the location of the target navigation device in the procedural field with the processor.

64. The method of clause 56, in which the step of defining the location of the robotic surgical apparatus in the coordinate system comprises:
using the spatial-data acquisition device to capture robot-location spatial data of the procedural field;
providing the robot-location spatial data to the processor;
identifying the robot navigation device with the processor; and
determining the location of the robotic surgical apparatus in the procedural field with the processor.

65. The method of clause 64, in which the step of illuminating the lighting structure with the lighting configuration comprises:
calculating, with the processor, a directional vector from the location of the robotic surgical apparatus in the coordinate system to the target location in the coordinate system; and
outputting a signal from the processor to the lighting structure that causes the lighting structure to be in the lighting configuration.

66. The method of clause 65, in which the lighting configuration includes at least one light source of the plurality of light sources that is illuminated and that is disposed closer to the target location in the procedural field than any light source of the plurality of light sources that is not illuminated.

67. The method of clause 65, in which the lighting configuration includes at least one light source of the plurality of light sources that is not illuminated and that is disposed closer to the target location in the procedural field than any light source of the plurality of light sources that is illuminated.

68. The method of clause 65, in which the lighting configuration includes at least one light source of the plurality of light sources that is illuminated in a first color and that is disposed closer to the target location in the procedural field than any light source of the plurality of light sources that is illuminated in a second color that is different than the first color.

69. The method of clause 68, in which all of the light sources of the plurality of light sources are illuminated in either first color or the second color.

70. The method of clause 68, in which the step of providing the signal that the robotic surgical apparatus is positioned at the target location includes illuminating all of the plurality of light sources.

71. The method of clause 70, in which the step of providing the signal that the robotic surgical apparatus is positioned at the target location includes illuminating all of the plurality of light sources in a third color that is different from the first color and the second color.

72. The method of clause 71, in which the first color comprises blue, the second color comprises red, and the third color comprises green.

73. The method of clause 64, in which the spatial data acquisition device comprises a camera and the spatial data comprises an image captured by the camera.

Any of the examples, clauses, or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of positioning a robotic surgical apparatus comprising a light ring including a plurality of light sources distributed 360 degrees about the light ring, the method comprising:
defining a coordinate system representative of a procedural field having a reference point;
defining a target location in the coordinate system representative of a target location in the procedural field;
defining a first location of the robotic surgical apparatus in the coordinate system representative of a first location of the robotic surgical apparatus in the procedural field;
calculating a directional vector from the first location of the robotic surgical apparatus in the coordinate system to the target location in the coordinate system;

illuminating the light ring with a lighting configuration comprising an illuminated portion that points toward the target location in the procedural field along a direction from the first location of the robotic surgical apparatus in the procedural field toward the target location in the procedural field, the direction in the procedural field corresponding to the directional vector in the coordinate system;

updating the lighting configuration to an updated lighting configuration in which an illuminated portion of the updated lighting configuration is larger than the illuminated portion of the lighting configuration, and in which the updated lighting configuration points in an updated direction from a second location of the robotic surgical apparatus in the procedural field toward the target location in the procedural field, the second location of the robotic surgical apparatus in the procedural field being closer to the target location in the procedural field than the first location of the robotic surgical apparatus in the procedural field, such that the updated lighting configuration also indicates that the second location of the robotic surgical apparatus in the procedural field is closer to the target location than the first location of the robotic surgical apparatus in the procedural field; and updating the updated lighting configuration to a target lighting configuration in which an illuminated portion of the target lighting configuration is larger than the illuminated portion of the updated lighting configuration such that the target lighting configuration provides an indication that the robotic surgical apparatus is positioned at the target location in the procedural field.

2. The method of claim 1, in which the plurality of light sources are distributed between every one degree to every four degrees about the light ring.

3. The method of claim 2, in which the light ring comprises a translucent housing component that covers the plurality of light sources such that light from the plurality of light sources passes through the translucent housing component and such that the plurality of light sources are not visible through the translucent housing component.

4. The method of claim 3, in which the illuminated portion of the lighting configuration is illuminated by a first number of the plurality of light sources, the illuminated portion of the updated lighting configuration is illuminated by a second number of the plurality of light sources that is greater than the first number of the plurality of light sources, and the illuminated portion of the target lighting configuration is illuminated by a third number of the plurality of light sources that is greater than the second number of the plurality of light sources.

5. The method of claim 4, in which the third number of the plurality of light sources comprises an entirety of the plurality of light sources.

6. The method of claim 2, in which the step of defining the coordinate system comprises:
using a spatial-data acquisition device to collect reference spatial data of the procedural field that includes the reference point;
providing the reference spatial data to a processor;
identifying the reference point with the processor; and
defining an origin representative of the reference point in the procedural field.

7. The method of claim 6, further comprising positioning a reference navigation device at the reference point in the procedural field such that the step of identifying the reference point with the processor includes identifying the reference navigation device.

8. The method of claim 2, further comprising positioning a target navigation device at the target location in the procedural field.

9. The method of claim 8, in which the step of defining the target location in the coordinate system comprises:
using a spatial-data acquisition device to capture target spatial data of the procedural field;
providing the target spatial data to the processor;
identifying the target navigation device with the processor; and
determining the location of the target navigation device in the procedural field with the processor.

10. The method of claim 9, in which the step of defining the first location of the robotic surgical apparatus in the coordinate system comprises:
using the spatial-data acquisition device to capture robot-location spatial data of the procedural field;
providing the robot-location spatial data to the processor;
identifying a robot navigation device of the robotic surgical apparatus with the processor; and
determining the initial location of the robotic surgical apparatus in the procedural field with the processor.

11. The method of claim 10, in which the step of illuminating the light ring with the lighting configuration comprises:
outputting a signal from the processor to the light ring that causes the light ring to be in the lighting configuration.

12. The method of claim 11, in which the illuminated portion of the lighting configuration is illuminated by at least one light source of the plurality of light sources that is illuminated in a first color and at least one light source of the plurality of light sources that is illuminated in a second color, the at least one light source that is illuminated in the first color being disposed closer to the target location in the procedural field than the at least one light source that is illuminated in the second color, the second color being different than the first color.

13. The method of claim 12, in which the illuminated portion of the target lighting configuration is illuminated by at least one light source of the plurality of light sources that is illuminated in a third color that is different from the first color and different from the second color.

14. The method of claim 13, in which the first color comprises blue, the second color comprises red, and the third color comprises green.

15. The method of claim 10, in which the spatial data acquisition device comprises a camera and the spatial data comprises an image captured by the camera.

* * * * *